United States Patent [19]

Nakano et al.

[11] Patent Number: 5,585,507

[45] Date of Patent: Dec. 17, 1996

[54] ALKYLSULFONIUM SALTS AND PHOTORESIST COMPOSITIONS CONTAINING THE SAME

[75] Inventors: Kaichiro Nakano; Katsumi Maeda; Shigeyuki Iwasa; Etsuo Hasegawa, all of Tokyo, Japan

[73] Assignee: NEC Corporation, Tokyo, Japan

[21] Appl. No.: 478,969

[22] Filed: Jun. 7, 1995

Related U.S. Application Data

[62] Division of Ser. No. 274,436, Jul. 13, 1994.

[30] Foreign Application Priority Data

Jul. 14, 1993 [JP] Japan .................................. 5-174528
Jul. 14, 1993 [JP] Japan .................................. 5-174532

[51] Int. Cl.$^6$ .............................. C07F 5/02; C07F 9/66; C07F 9/90; C07C 381/12
[52] U.S. Cl. .............................. 556/7; 556/64; 562/113; 568/1; 568/77
[58] Field of Search .............................. 568/77.1; 556/64, 556/7; 562/113

[56] References Cited

U.S. PATENT DOCUMENTS

| 5,191,124 | 3/1993 | Schwalm et al. ........................ 568/18 |
| 5,230,984 | 7/1993 | Tachiki et al. .......................... 430/270 |
| 5,247,113 | 9/1993 | Roth et al. ............................... 556/64 |
| 5,466,845 | 11/1995 | Herzig ..................................... 556/12 |

OTHER PUBLICATIONS

C. W. Wilkins, Jr. et al., "An organosilicon novalac resin for multilevel resist applications", *Journal of vacuum Science and Technology*, B3(1), Jan./Feb. 1985, pp. 306–309.

Ito et al., "Applications of Photoinitiators to the Design of Resists for Semiconductor Manufacturing", *American Chemical Society Symposium Series*. vol. 242, 1984, pp. 11–23.

J. Crivello et al., "A New Preparation of Triarylsulfonium ... Selenides with Diaryliodonium Salts", *Journal of Organic Chemistry*, vol. 43, No. 15, 1978, pp. 3055–3058.

Neenan et al., "Chemically Amplified Resists: A Lithographic Comparison of Acid Generating Species", *Proceedings of SPIE*, vol. 1086, pp. 2–10.

Ueno et al., "Chemical Amplification Positive Resist Systems Using Novel Sulfonates as Acid Generators", *Proceedings of PME '89*, Kohdansha Co., 1990, pp. 413–424.

Takechi et al., "Alicyclic Polymer for ArF and KrF Excimer Resist Based on Chemical Amplification", *Journal of Photopolymer Science and Technology*, vol. 5, No. 3, 1992, pp.439–446.

D. N. Kevill et al., "Essentially Solvent–Independent ... and the $N_{k1}$ Solvent Nucleophilicity Scale", *Journal of the American Chemical Society*, vol. 108, No. 7, 1986, pp. 1579–1585.

G. L. Gaines, Jr., "Solvatochromic Compound as an Acid Indicator in Nonaqueous Medial", *Analytical Chemistry*, vol. 48, No. 2, Feb. 1976, pp. 450–451.

*Primary Examiner*—Gary Geist
*Assistant Examiner*—Dwayne C. Jones
*Attorney, Agent, or Firm*—Sughrue, Mion, Zinn, Macpeak & Seas

[57] ABSTRACT

A photoresist composition containing an alkylsulfonium salt compound represented by the following general formula (I):

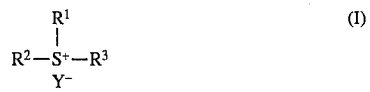

Wherein $R^1$ and $R^2$ may be the same or different, each being a linear, branched or cyclic $C_1$ to $C_8$ alkyl radical, $R^3$ is a linear, branched or cyclic $C_1$ to $C_8$ alkyl radical, a $C_5$ to $C_7$ 2-oxocycloalkyl radical, or a linear or branched $C_3$ to $C_8$ 2-oxoalkyl radical, and $Y^-$ represents a counter ion. The photoresist composition has high transparency to deep U.V. light having wavelengths of 220 nm or less and is capable of forming good fine patterns with high sensitivity, thus being useful as chemically amplified type resist which is exposed to the deep U.V. light from an ArF excimer laser.

9 Claims, 2 Drawing Sheets

5,585,507

ALKYLSULFONIUM SALTS AND PHOTORESIST COMPOSITIONS CONTAINING THE SAME

This is a divisional of application Ser. No. 08/274,436 filed Jul. 13, 1994.

BACKGROUND OF THE INVENTION

1. Field of the Invention

The present invention relates to a novel alkylsulfonium salt and a novel photoresist composition containing the same or the other alkylsulfonium salt, and in particular to a novel alkylsulfonium salt to which deep U.V. light having wavelengths of 220 nm or less is less absorbed and which generates efficiently photoacids (i.e. protonic acids) and a novel photoresist composition which contains the same or the other alkylsulfonium salt and is suitable for exposure to the deep U.V. light having the wavelengths of 220 nm or less.

2. Disclosure of the Related Art

Recently, in the field of semiconductor devices, integrated circuits and the other various electronic devices in which fine processing has been required, photoresists have been extensively used and highly densified and integrated devices have been desired increasingly. Thus, requirements for a photolithography technology which is used to realize a fine patterning have become increasingly strict.

Such fine patterning has been performed by using exposure light having shorter wavelengths in patterning of the photoresist. In general, resolution (line width) R in the optical system is defined in terms of Rayleigh's equation:

$$R = k \cdot \lambda / NA$$

wherein $\lambda$ represents a wavelength of a light source for exposure, NA represents numerical aperture of lens and k represents a process factor. It is seen from this equation that higher resolution, i.e. a small value of R, is attained by shortening the wavelength $\lambda$ of the exposure light in a photolithography. For instance, in manufacturing a dynamic random access memory (hereinafter referred to as "DRAM") having level of integration up to 64 M, the degree of resolution of the minimum pattern size 0.35 µm line-and-space has been required and for this reason, a g-line (438 nm) or i-line (365 nm) of a high-pressure mercury vapor lamp has been used as a light source up to date. However, in manufacturing DRAM having level of integration of 256 M or more in which even finer processing techniques (processing size of 0.25 µm or less) are required, it is believed that the light having shorter wavelengths (deep U.V. light etc.), such as excimer laser beams (KrF: 248 nm, KrCl: 222 nm, ArF: 193 nm, $F_2$: 157 nm) can be effectively used, as taught in T. Ueno et el., Short Wavelength Photoresist Materials- Fine Processing for ULSI, Publisher Bunshin, 1988. Particularly, KrF lithography is investigated actively at the present time.

With regard to the photoresists, high integration has been investigated on the basis of multilayer (two or three layers) resist processes in place of conventional single-layer resist processes. As for the two-layer resists, there are known, for instance, resists (two-layer resists having silylated novolak resin as the upper layer) described in Wilkins et al., Journal of Vacuum Science and Technology, B3, 306–309, 1985.

With regard to resist materials for use in the fine processing, the requirements for high sensitivity to exposure light have increased in addition to high resolution corresponding to reduction in the processing size. This is based on the fact that it is necessary to realize improvement in cost performance of the laser because gas life of the excimer laser as the light source is short and the laser itself is expensive. In order to attain high sensitivity of the resist to light, chemically amplified type resists in which a photoacid generator is utilized as a photosensitizer have been developed and investigated in detail as resist for use in the KrF excimer laser as described in H. Ito and C. Grant Willson, American Chemical Society Symposium Series, Vol. 242, pp. 11–23, 1984. The photoacid generator means a material for generating an acid by light irradiation. In the chemically amplified type resist containing the photoacid generator, a protonic acid generated by the photoacid generator is moved to solid phase of the resist in the course of a post-exposure baking treatment and thus amplifies catalytically chemical change in the resist material several hundred times to several thousand times. This resist attains remarkably high sensitivity as compared with the conventional resist having photoreaction efficiency below 1 (reaction efficiency per one photon). As for the photoacid generator for use in the chemically amplified type resist, there were known, for instance, triphenylsulfonium salt derivatives described in J. V. Crivello et al., Journal of the Organic Chemistry, Vol. 43, No. 15, pp. 3055–3058, 1978; 2,6-dinitrobenzyl esters described in T. X. Neenan et al., Proceedings of SPIE, Vol.1086, pp. 2–10, 1989; and 1,2,3-tri(methanesulfonyloxy)benzene described in T. Ueno et al., Proceedings of PME"89, Kohdansha Co., pp. 413–424, 1990.

Most of the resists under development at the present time are such chemically amplified type resists. The development of high photosensitive materials corresponding to shortened wavelengths of the exposure source is essentially performed on the basis of the utilization of chemical amplification mechanism.

The chemically amplified type resist for exposure to light from the KrF excimer laser needs transmittance of 60% or more per 1 µm in thickness. In such resist, the transmittance at the exposure wavelength is important to resolve the pattern.

However, even if the chemically amplified type single-layer resist for exposure to the g-line, i-line or KrF excimer laser beams which is broadly used at the present time is exposed to the light having wavelengths shorter than 220 nm, for instance, to the ArF excimer laser beams (193 nm), generally the pattern cannot be resolved because of very strong absorption of the light to the resist. Namely, in the single-layer resist having a thickness of about 0.71–1.0 µm, the exposure light is mostly absorbed to the resist in the vicinity below its surface at the incident side of light and thus the light does not almost reach a portion of the resist near the substrate. As a result, the portion of the resist near the substrate is not almost exposed to light and thus the patterns are not resolved. For this reason, in the photolithography in which an ArF excimer laser expected as the light source of the next generation following the KrF excimer laser is used, the existing resists are not exposed to light and thus the patterns are not quite resolved. The conventional photoacid generators including Crivello et al.'s triphenylsulfonium salt derivatives which are contained in the chemically amplified type resist as mentioned above absorb greatly the exposure light having wavelengths of 220 nm or less because all these compounds have an aromatic ring in their structure. For the above-mentioned reason, the existing photoacid generators cannot be applied to the chemically amplified type resists which are exposed to the exposure light having wavelengths of 220 mn or less with which higher resolution of the pattern can be expected.

With regard to a polymer to be used as a base of the resist, there are the same problems as in the photoacid generator. Both the polymer such as novolak resin which is used in most of the existing resist for i-line and poly(p-vinylphenol) which is broadly used at the present time as a basic polymer of the chemically amplified type resist for exposure to the KrF excimer laser beam have an aromatic ring in their molecular structure. This is based on the fact that it is necessary to include a number of strong unsaturated bonds in the molecular structure of the resist in order to attain sufficient resistance of the resist to a dry etching process following the patterning process in a method of fabricating the semiconductor device. Thus, the aromatic ring was included in the polymer for resist as necessary and indispensable structure for sufficiently attaining the intended object. As mentioned above, the requirements for fine processing have become increasingly strict and further reduction in size of the pattern has been investigated. As for the resist for use in the KrF excimer laser as the light source having shorter wavelengths than in the i-line, poly(p-vinylphenol) has been broadly used in place of the novolak resin having strong absorption at 248 nm. This resin is transparent to the KrF excimer laser beam (248 nm) (transmittance is of the order of about 70% when the film thickness is 1 μm) but has strong absorption at the wavelength region shorter than 248 nm because of the aromatic ring included in its structure. Thus, the resin cannot be utilized as the resist for lithography in which the light of shorter wavelengths than in KrF, in particular the light having wavelengths of 220 nm or less is used as the exposure light. As for the resin which is transparent at the wavelength region of 220 nm or less, there is a methacrylic resin, for instance, poly(methyl methacrylate) or the like. Though polymers which include no aromatic ring in the molecular structure exhibit the transparency to the light of 220 nm or less, such polymers exhibit no resistance to the above dry etching process and, as a result, cannot be utilized as the photoresist. In order to solve this problem, there is provided resist comprising an alicyclic polymer as reported in Takechi et al., Journal of Photopolymer Science and Technology, Vol. 5, No. 3, pp. 439–446, 1992. In the report, a copolymer of poly(adamantyl methacrylate) and poly(tert-butyl methacrylate) has been proposed as a polymer having the transparency to the light at 193 nm and the dry etching resistance.

As mentioned above, the polymers for use in the lithography which is carried out at the wavelengths of 220 nm or less were reported in a few publications but the photoacid generator which can be combined with these polymers and is necessary and indispensable to develop a chemical amplification action essential for improvement in cost performance of the laser was reported in no publication.

SUMMARY OF THE INVENTION

Accordingly, an object of the present invention is to provide a novel chemically amplified type photoresist composition containing an alkylsulfonium salt compound as a photoacid generator which has high transparency to deep U.V. light of 220 nm or less and high photoreaction efficiency (high photoacid generation efficiency).

Another object of the present invention is to provide a novel photoacid generator having less absorption to deep U.V. light of 220 nm or less and high photoreaction efficiency (high photoacid generation efficiency).

According to one aspect of the present invention, there is provided a chemically amplified type photoresist composition containing an alkylsulfonium salt compound having the following general formula (I):

wherein $R^1$ and $R^2$ may be the same or different, each being a linear, branched or cyclic $C_1$–$C_8$ alkyl radical, $R^3$ is a radical selected from the group consisting of a linear, branched or cyclic $C_1$–$C_8$ alkyl radical, a $C_5$–$C_7$ 2-oxocycloalkyl radical and linear or branched $C_3$–$C_8$ 2-oxoalkyl radical and $Y^-$ represents a counter ion.

In the above general formula (I), $R^1$, $R^2$ and $R^3$ may be the same or different. In these substituents, the linear, branched and cyclic $C_1$–$C_8$ alkyl radicals include, for instance, methyl, ethyl, n-propyl, i-propyl, n-butyl, i-butyl, sec-butyl, tert-butyl, pentyl, hexyl, heptyl, octyl, cyclopentyl, cyclohexyl, cycloheptyl, cyclopropylmethyl, 4-methylcyclohexyl and cyclohexylmethyl radicals or the like.

In $R^3$, the $C_5$–$C_7$ 2-oxocycloalkyl radical includes, for instance, 2-oxocyclopentyl, 2-oxocyclohexyl and 2-oxocycloheptyl radicals or the like, and the linear and branched $C_3$–$C_8$ 2-oxoalkyl radicals include, for instance, 2-methyl-2-oxoethyl, 2-ethyl-2-oxoethyl, 2-isopropyl-2-oxoethyl and 2-hexyl-2-oxoethyl radicals or the like.

As for $R^1$ and $R^2$, the above-mentioned radicals are generally effective and at least one of $R^1$ and $R^2$ is preferably the cyclic alkyl radical from a characteristic standpoint such as very excellent thermal stability (starting temperature of thermal decomposition is high) and high melting point.

As for $R^3$, the above-mentioned radicals are generally effective and the linear, branched and cyclic 2-oxoalkyl radicals are preferred from a characteristic standpoint such as very high photoreaction efficiency (high photoacid generation efficiency).

$Y^-$ includes, for instance, the counter ions such as $BF_4^-$ (tetrafluoroborate ion), $AsF_6^-$ (hexafluoroarsenate ion), $SbF_6^-$ (hexafluoroantimonate ion), $PF_6^-$ (hexafluorophosphate ion), $CF_3SO_3^-$ (trifluoromethanesulfonate ion), $Cl^-$ (chlorine ion), $Br^-$ (bromine ion), $I^-$ (iodine ion), $ClO_4^-$ (perchloric ion), $CH_3SO_3$ (methanesufonate ion) and the like. It is preferred that $Y^-$ is $BF_4^-$, $AsF_6^-$, $SbF_6^-$, $PF_6^-$ or $CF_3SO_3^-$ ion from the point of view of suppressing of contamination with impurity ions in the course of a process for fabricating integrated circuits, and suppressing scattering and disappearance of the protonic acid from the resist in the course of post exposure baking treatment which is applied in forming the resist patterns.

The alkylsulfonium salt derivatives of the general formula (I) of the present invention can be prepared, for instance, according to a D. N. Kevill et al. 's method relating to the preparation of sulfonium salts described in Journal of the American Chemical Society, Vol. 108, No. 7, pp. 1579–1585, 1986. Namely, an excess of halogenated alkyl represented by the following general formula (II) or (III):

$$R^2\text{-}W \qquad (II)$$

or $$R^1\text{-}W \qquad (III)$$

wherein $R^1$ and $R^2$ are as defined above and W represents a halogen atom such as iodine, bromine, chlorine or the like, is added to a solution of a sulfide derivative represented by the following general formula (IV) or (V):

$$R^3\text{-}S\text{-}R^1 \qquad (IV)$$

or $$R^3\text{-}S\text{-}R^2 \quad (V)$$

wherein $R^1$, $R^2$ and $R^3$ are as defined above, in a solvent. The mixture is allowed to react at room temperature for 0.5–5 hours, preferably for 1–2 hours. Then, a solution of a metal salt of organic acid represented by the following general formula (VI):

$$M^+ Y^- \quad (VI)$$

wherein $M^+$ represents $K^+$, $Na^+$ or $Ag^+$ and $Y^-$ is as defined above, in nitromethane is added to the reaction mixture, an amount of the organic metal salt equaling in mole to the sulfide derivative. The mixture is allowed to react at room temperature to 50° C. for 3 to 24 hours. Thereafter, insoluble metal salts are removed from the reaction mixture by filtration. The filtrate is concentrated and then poured into a bulk of poor solvent such as diethyl ether to reprecipitate a crude product. The precipitate thus obtained is recrystallized from a suitable solvent such as ethyl cellosolve acetate or the like to obtain a final alkylsulfonium salt derivative (formula (I)).

The solvent for the sulfide derivative includes, for instance, nitromethane or the like. An amount of halogenated alkyl to be used is generally 2 to 10 times as much as mole of the sulfide derivative and preferably 5 to 20 times.

The photoacid generator, i.e. triphenylsulfonium trifluoromethanesulfonate (hereinafter referred to as "TPS"), which was developed for use in the KrF excimer laser lithography by J. V. Crivello et al. and described in the above-mentioned their article, cannot be used as a constituent ingredient of resist for use in the ArF excimer laser lithography because the photoacid generator has very remarkable light absorption at the deep U.V. light region of 220 nm or less. In comparison with the TPS, all the above-mentioned sulfonium salt derivatives for use in the present invention have remarkably less absorption at the deep U.V. light region of 185.5 to 220 nm. Thus, it will be apparent that the sulfonium salt derivatives for use in the present invention can be used as a constituent ingredient of resist for use in ArF excimer laser lithography from the standpoint of transparency to the exposure light. It is confirmed that the protonic acid is generated by irradiating the alkyl-sulfonium salt derivatives in the present invention with the radiation such as the deep U.V. light, excimer laser beams or the like.

The photoresist composition of the present invention comprises the alkylsulfonium salt compound, polymer and solvent as constituent elements.

In the photoresist composition of the present invention which contains the alkylsulfonium salt compound represented by the general formula (I), the alkylsulfonium salt compound may be used alone or in combination (i.e. as a mixture of two or more). In the photoresist composition of the present invention, the content of the alkylsulfonium salt compound represented by the general formula (I) is ordinarily 0.1 to 40 parts by weight and preferably 1 to 25 parts by weight, based on 100 parts by weight of all solid content including the compound. If the content is less than 0.1 parts by weight, sensitivity to light is reduced remarkably and thus it is difficult to form the pattern. In addition, if the content is beyond 40 parts by weight, it is difficult to form a uniform coating film and further scum is easily produced after development.

The polymer serving as the constituent element of the present invention can be selected appropriately from polymers having high transparency at the deep U.V. light region of 220 nm or less and having any functional group and any radical instable to acid. For instance, it is possible to use polymers represented by the following general formula (VII):

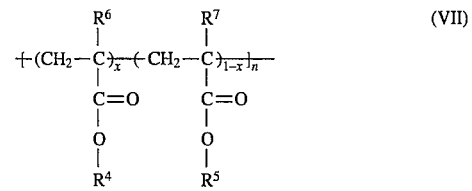

wherein n is a positive integer of 5 to 1,000, preferably 10 to 200, $R^4$ represents a tricyclodecanyl tricyclodecenyl tricyclodecenyloxyethyl, cyclohexyl, norbornyl or adamantyl radical as shown in Table 1, $R^5$ represents a methyl, ethyl, propyl, tert-butyl, tetrahydropyranyl or 3-oxocyclohexyl radical, and x is 0.1 to 1, preferably 0.2 to 0.7, $R^6$ and $R^7$ may be the same or different and represent hydrogen or a $C_1$ to $C_3$ lower alkyl radical such as methyl, ethyl or propyl radical.

TABLE 1

| $R^4$ | Chemical Structure of Radical |
|---|---|
| Tricyclodecanyl Radical | |
| Tricyclodecenyl Radical | |
| Tricyclodecenyloxyethyl Radical | $-CH_2CH_2-O-$ |
| Cyclohexyl Radical | |
| Norbornyl Radical | |
| Adamantyl Radical | |

Furthermore, it is possible to use a polymer mixture containing a plurality of polymers of the above formula (VII) as the constituent elements in the present invention. A solvent to be used in the present invention is not particularly limited and preferably includes any organic solvent in which the elements such as the polymer, the alkylsulfonium salt and the like are sufficiently dissolved so that a uniform coating film can be formed by application of the resulting solution according to a spin coating method. The organic solvent includes, for instance, alcohol such as n-propyl alcohol, isopropyl alcohol, n-butyl alcohol, tert-butyl alcohol or the like; acetate such as methyl cellosolve acetate, ethyl cellosolve acetate, propyleneglycol monoethylether acetate or the like; lactate such as methyl lactate, ethyl lactate or the like; acetate such as 2-methoxybutyl acetate, 2-ethoxyethyl acetate or the like; pyruvate such as methyl pyruvate, ethyl pyruvate or the like; propionate such as methyl 3-methoxypropionate, ethyl 3-methoxypropionate or the like; ketones such as N-methly -2-pyrrolidinone, cyclohexanone, cyclopentanone, methylethylketone or the like; cyclic alcohol such as cyclohexanol, cyclopentanol or the like; or ethers such as 1,4-dioxane, ethylene glycol monomethyl ether, ethylene glycol monomethyl ether acetate, ethylene glycol monoethyl ether, ethylene glycol monoisopropyl ether, diethylene glycol monomethyl ether, diethylene glycol dimethyl ether or the like. Of course, the solvent for use in the present invention is not limited to the above-mentioned solvents, namely all the organic solvents, in which the constituent elements of the composition of the present invention are sufficiently dissolved and which are capable of forming the film, can be used to attain the object of the present invention.

The photoresist composition of the present invention comprises basically the above-mentioned alkylsulfonium salt compound, polymer and solvent but the other elements such as a surfactant, colorant (dye, pigment), stabilizer, coating modifier and/or crosslinking agent or the like may be added to the composition according to need.

In addition, as for a developing solution in the fine patterning process using the photoresist composition of the present invention, any appropriate organic solvent or its combined solvent or an alkali solution or aqueous alkali solution having appropriate alkali concentration can be selected according to solubility of the polymer used in the present invention therein. The organic solvent to be used is not particularly limited and includes, for instance, ketones such as acetone, methylethylketone or the like; alcohol such as methyl alcohol, ethyl alcohol, isopropyl alcohol or the like; or ethers such as tetrahydrofuran, dioxane or the like; or a mixture thereof. The alkali solution to be used is not particularly limited and includes, for instance, a solution or an aqueous solution containing an inorganic alkali such as sodium hydroxide, potassium hydroxide, sodium silicate, ammonia or the like; an organic amine such as ethylamine, propylamine, diethylamine, dipropylamine, trimethylamine, triethylamine or the like; or an organic ammonium salt such as tetramethylammonium hydroxide, tetraethylammonium hydroxide, trimethylhydroxymethylammonium hydroxide, triethylhydroxymethylammonium hydroxide, trimethylhydroxyethylammonium hydroxide or the like; or a mixture thereof.

According to another aspect of the present invention, there is provided a novel alkylsulfonium salt compound as mentioned below.

Among the above-mentioned alkylsulfonium salt compounds represented by the general formula (I), the compounds of the formula (I), in which $R^1$ and $R^2$ may be the same or different, $R^1$ is a linear, branched or cyclic $C_1$–$C_8$ alkyl radical, $R^2$ is a $C_5$ to $C_7$ cycloalkyl radical, $R^3$ is a $C_5$–$C_7$ 2-oxocycloalkyl radical and $Y^-$ is as defined above, are novel and have less absorption to the deep U.V. light having wavelengths of 220 nm or less and generate effectively the protonic acid, as mentioned above.

In these novel alkylsulfonium salt compounds, the linear, branched and cyclic $C_1$ to $C_8$ alkyl radicals and $C_5$ to $C_7$ 2-oxocycloalkyl radical includes, for instance, the radicals as defined above. The $C_5$ to $C_7$ cycloalkyl radical includes, for instance, a cyclopentyl, cyclohexyl, cycloheptyl, 4-methylcyclohexyl or cyclohexylmethyl radical or the like as mentioned above.

The novel alkylsulfonium salt compounds in the present invention include, for instance, the following compounds:

cyclohexylmethyl(2-oxocyclohexyl) sulfonium trifluoromethanesulfonate;

dicyclohexyl(2-oxocyclohexyl)sulfonium trifluoromethanesulfonate;

cyclopentylmethyl(2-oxocyclohexyl)sulfonium trifluoromethanesulfonate; and cycloheptylmethyl(2-oxocyclopentyl)sulfonium trifluoromethanesulfonate.

Of course, the novel alkylsulfonium salt compounds are prepared in the same manner as mentioned above and have the same light absorption as mentioned above, and also generate the protonic acid in the same manner.

Thus, these novel compounds can be utilized as an initiator of cationic photopolymerizaton using light having short wavelengths and as a sensitizer for photoresist as discussed above. Of course, the photoresist compositions containing these compounds are prepared in the same manner as mentioned above.

In each of the above-mentioned substituents in these novel compounds, the number of carbon atom is most preferable values selected from the practical standpoint and the approximately similar effect can be attained even if the number is beyond the above values, for instance, even if the number of carbon atom is 9 or more in $R^1$ and 3–4 and 8 or more in $R^2$ and $R^3$.

In the present invention, the coating film obtained from the photoresist composition is exposed to the deep U.V. light from the ArF excimer laser or the like, the compound of the general formula (I) including the novel compound which is contained in the exposed portion of the coating film generates the acid according to the following reaction scheme (VIII):

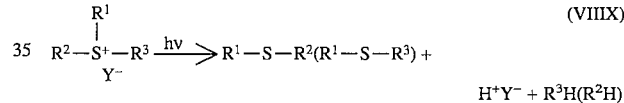

wherein $R^1$ $R^2$ $R^3$ and $Y^-$ are as defined in the general formula (I).

In the present invention, for instance, if the polymer represented by the general formula (VII) wherein $R^5$ is a tert-butyl radical is used, the protonic acid generated by light irradiation brings about chemical change in the tertbutyloxy radical in the polymer according to the following reaction scheme (IX) to form a carboxylic group and 2-butene and thus induce change in solubility of the resist.

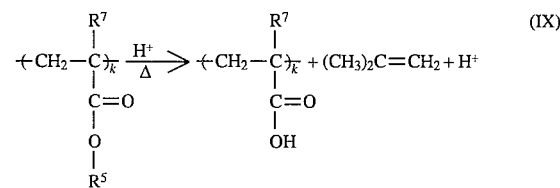

wherein k is a positive integer and $R^5$ is a defined in the general formula (VII).

If the post exposure baking following the exposure to light is carried out at any prescribed temperature, this elimination reaction of a protective group takes place catalytically and thus the sensitivity is amplified. The polymer in which the functional group changed to the hydroxyl group according to this reaction is soluble in alkali. Thus, the polymer flows out by using an alkaline developing solution and as a result, the exposed portion is dissolved to form a positive type pattern.

As discussed in the following Examples, it was confirmed that the protonic acid was generated by irradiating the above-mentioned alkylsulfonium salt with the deep U.V. light such as the ArF excimer laser beams having a wavelength of 193 nm.

Furthermore, if the photoresist composition of the present invention is applied as shown in the Examples, it was confirmed from resolution experiments using, for instance, the ArF excimer laser beams as the exposure light that a good rectangular fine pattern was formed with high sensitivity.

Namely, the composition containing the alkylsufonium salt derivative in the present invention as the constituent element can be utilized as photoresist for forming the fine patterns in the lithography in which the deep U.V. light having wavelengths of 220 nm or less is used as the exposure light.

The foregoing and other objects and features of the present invention will be apparent from the following description.

DETAILED DESCRIPTION OF THE PREFERRED EMBODIMENTS

Figure 1:
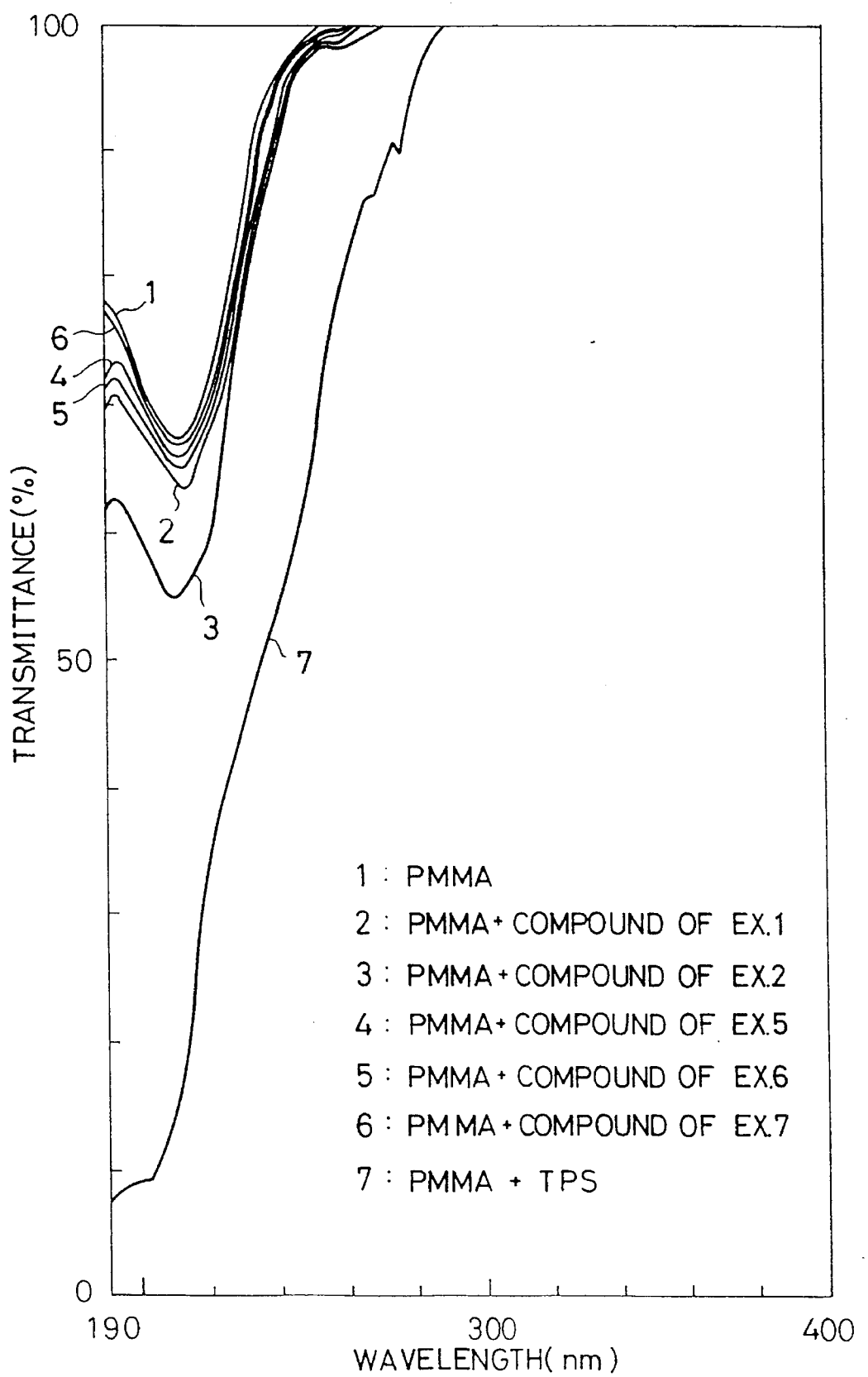
FIG. 1 is a diagram showing dependence of transmittance of each of seven films obtained in Example 8 (film-forming materials: compounds of Examples 1, 2, 5, 6 and 7; PMMA; and PMMA+TPS) on wavelengths which was determined using an ultraviolet visible spectrophotometer.

The present invention will be hereinafter described in more detail with reference to the non-limiting working Examples given by way of illustration and the effects practically achieved by the present invention will also be discussed in more detail in comparison with Control Example.

EXAMPLE 1

Preparation of cyclohexylmethyl (2-oxocyclohexyl) sulfonium trifluoromethanesulfonate:

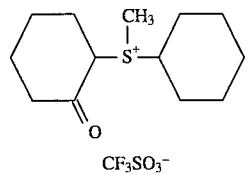

$CF_3SO_3^-$

The following preparation was carried out under a yellow lamp.

10.0 g (41.1 mmol) of 2-(cyclohexylmercapto)cyclohexanone was dissolved in 30 ml of nitromethane in a 300 ml round bottomed glass flask and stirred with a Teflon stirring bar/magnetic stirrer. To the solution, 54 g (380 mmol) of methyl iodide was added with a dropping funnel and, at the end of dropping, stirred at room temperature for one hour. Then, to the resulting solution, a solution of 12.1 g (41.1 mmol) of silver trifluoromethanesulfonate in 200 ml of nitromethane was gradually added dropwise with a dropping funnel. After stirring for 15 hours, deposited silver iodide was separated by filtration and the nitromethane solution was concentrated into 20 ml. The nitromethane solution thus concentrated was poured into 200 ml of diethyl ether to precipitate a crystal. The crystal thus deposited was washed with diethyl ether several times and thereafter the residue was recrystallized from ethyl cellosolve acetate to obtain 11.2 g (yield: 63%) of a final product. Structure Of the final product was identified by a $^1$H-NMR measurement (an AMX-400 type NMR apparatus manufactured by Bruker Co.), an IR measurement (IR-470 manufactured by Shimadzu Co.) and elemental analysis. Thermal analysis was performed by a Thermal Analysis System 001 (Mack Science Co.). Melting Point: 91°–93° C. $^1$H-NMR (CDCl$_3$, internal standard: tetramethylsilane):

δ(ppm)

1.22–1.35(m, 1H), 1.40–1.78(m, 6H), 1.84–2.27(m, 8H), 2.54–2.64(m, 2H), 2.70–2.80(m, 1H), 2.81(s, 1.5H), 2.92(s, 1.5H), 3.62(tt, 0.5H), 3.73(tt, 0.5), 5.17(t, 0.5H), 5.18(t, 0.5H)

IR (KBr tablet, cm$^{-1}$)

2950, 2870($v_{C-H}$), 1710($v_{C=O}$), 1450($v_{C-H}$), 1276, 1256($v_{C-F}$), 1148, 1034($v_{SO_3}$)

| Elemental Analysis: | | C | H | S |
|---|---|---|---|---|
| Found | (% by weight): | 44.43 | 6.38 | 16.84 |
| Calculated | (% by weight): | 44.67 | 6.16 | 17.03 |

(The calculated values are based on $C_{14}H_{23}O_4S_2F_3$(MW: 376.4485) Starting Temperature of Thermal Decomposition: 142° C.

EXAMPLE 2

Preparation of dicyclohexyl (2-oxocyclohexyl) sulfonium trifluoromethanesulfonate:

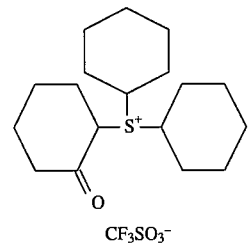

$CF_3SO_3^-$

In this Example, the same procedures as used in Example 1 were repeated to synthesize a desired final product, except that methyl iodide was replaced with cyclohexyl iodide. The final product had yield of 13%. Structure of the final product was identified by the same analysis method as in Example 1. Melting Point: 172°–174° C.

$^1$H-NMR (CDCl$_3$, internal standard: tetramethylsilane):

δ (ppm)

0.97–2.3(m, 24H), 2.33–2.80(m, 4H), 3.97–4.47(m, 2H), 5.20–5.35(m, 1H)

IR (KBr tablet, cm$^{-1}$)

2932, 2860($v_{C-H}$), 1700($v_{C=O}$), 1444($v_{C-H}$), 1276, 1256($v_{C-F}$), 1168, 1050($v_{SO_3}$)

| Elemental Analysis: | | C | H | S |
|---|---|---|---|---|
| Found | (% by weight): | 51.58 | 6.75 | 14.74 |
| Calculated | (% by weight): | 51.33 | 7.03 | 14.42 |

(The calculated values are based on $C_{19}H_{31}O_4S_2F_3$(MW: 444.5667)

Starting Temperature of Thermal Decomposition: 185° C.

EXAMPLE 3

Preparation of cyclopentylmethyl (2-oxocyclohexyl) sulfonium trifluoromethanesulfonate:

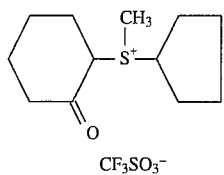

$CF_3SO_3^-$

In this example, the same procedures as in Example 1 were repeated to synthesize a desired final product, except that 2-(cyclohexylmercapto)cyclohexanone was replaced with 2-(cyclopentylmercapto)cyclohexanone- The final product had yield of 93% and was oily. Structure of the final product was identified by the same analysis method as in Example 1.

$^1$H-NMR (CDCl$_3$, internal standard: tetramethylsilane): δ (ppm)

1.50–2.50(m, 14H), 2.51–2.80(m, 2H), 2.85(s, 1.5H), 2.95(s, 1.5H), 3.67–4.23(m, 1H), 4.87–5.37(m, 1H)

IR (KBr tablet, cm$^1$)

2950, 2880($v_{C-H}$), 1710($v_{C=O}$), 1448, 1424($v_{C-H}$), 1264($v_{C-F}$), 1156, 1030(vhd SO$_3$)

| Elemental Analysis: | | C | H |
|---|---|---|---|
| Found | (% by weight): | 43.02 | 5.65 |
| Calculated | (% by weight): | 43.08 | 5.79 |

(The calculated values are based on $C_{13}H_{21}O_4S_2F_3$(MW: 362.4217)

EXAMPLE 4

Preparation of cycloheptylmethyl (2-oxocyclopentyl) sulfonium trifluoromethanesulfonate:

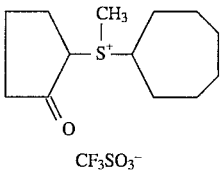

$CF_3SO_3^-$

In this example, the same procedures as in Example 1 were repeated to synthesize a desired final product, except that 2-(cyclohexylmercapto)cyclohexanone was replaced with 2-(cycloheptylmercapto)cyclopentanone. The final product had yield of 20%. Structure of the final product was identified by the same analysis method as in Example 1.

Melting Point: 97°–99° C.

| Elemental Analysis: | | C | H |
|---|---|---|---|
| Found | (% by weight): | 44.20 | 6.21 |
| Calculated | (% by weight): | 44.67 | 6.16 |

(The calculated values are based on $C_{14}H_{23}O_4S_2F_3$(MW: 376.4485)

EXAMPLE 5

Preparation of dimethyl(2-oxocyclohexyl)sulfonium trifluoromethanesulfonate:

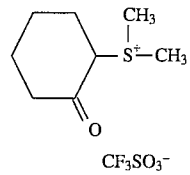

$CF_3SO_3^-$

In this example, the same procedures as in Example 1 were repeated to synthesize a desired final product, except that 2-(cyclohexylmercapto)cyclohexanone was replaced with 2-(methylmercapto)cyclohexanone. The final product had yield of 96% and was oily. Structure of the final product was identified by the same analysis method as in Example 1.

$^1$H-NMR (CDCl$_3$, internal standard: tetramethylsilane): δ (ppm)

1.47–2.83(m, 8H), 2.92(s, 3H), 3.02(s, 3H), 4.70–5.30(m, 1H)

IR (KBr tablet, cm$^{-1}$)

3032, 2988($v_{C-H}$), 1710($v_{C=O}$), 1450, 1428($v_{C-H}$), 1264($v_{C-F}$), 1160, 1030($v_{SO_3}$)

| Elemental Analysis: | | C | H |
|---|---|---|---|
| Found | (% by weight): | 35.46 | 5.23 |
| Calculated | (% by weight): | 35.06 | 4.90 |

(The calculated values are based on $C_9H_{15}O_4S_2F_3$(MW: 808.3808)

EXAMPLE 6

Preparation of methylpropyl (2-oxocyclohexyl) sulfonium trifluoromethanesulfonate:

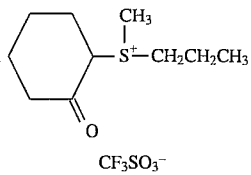

$CF_3SO_3^-$

In this example, the same procedures as in Example 1 were repeated to synthesize a desired final product, except that 2-(cyclohexylmercapto)cyclohexanone was replaced with 2-(propylmercapto)cyclohexanone. The final product had yield of 88% and was oily. Structure of the final product was identified by the same analysis method as in Example 1.

$^1$H-NMR (CDCl$_3$, internal standard: tetramethylsilane): δ (ppm)

1.13(t, 1.5H), 1.14(t, 1.5H), 1.65–2.05(m, 5H), 2.08–2.25(m, 2H), 2.57–2.71(m, 3H), 2.87(s, 1.5H), 2.97(s, 1.5H), 3.19–3.40(m, 2H), 5.13–5.18(m, 1H)

IR (KBr tablet, cm$^{-1}$)

2940, 2880($v_{C-H}$), 1710($v_{C=O}$), 1448, 1424($v_{C-H}$), 1260($v_{C-F}$), 1156, 1030($v_{SO_3}$)

| Elemental Analysis: | | C | H |
|---|---|---|---|
| Found | (% by weight): | 39.55 | 5.86 |
| Calculated | (% by weight): | 39.28 | 5.69 |

(The calculated values are based on C$_{11}$H$_{19}$O$_4$S$_2$F$_3$(MW: 336.3839)

EXAMPLE 7

Preparation of dicyclohexylmethylsulfonium trifluoromethanesulfonate:

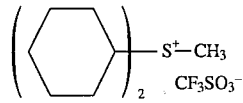

In this example, the same procedures as in Example 1 were repeated to synthesize a desired final product, except that 2-(cyclohexylmercapto)cyclohexanone was replaced with dicyclohexylsulfide. The final product had yield of 73%. Structure of the final product was identified by the same analysis method as in Example 1.

Melting Point: 52°–54° C.

$^1$H-NMR (CDCl$_3$, internal standard: tetramethylsilane): δ (ppm)

1.07–2.40(m, 20H), 2.82(s, 3H), 3.37–3.97(m, 2H)

IR (KBr tablet, cm$^{-1}$)

2940, 2860($v_{C-H}$), 1446($v_{C-H}$), 1261($v_{C-F}$), 1148, 1030($v_{SO_3}$)

| Elemental Analysis: | | C | H |
|---|---|---|---|
| Found | (% by weight): | 46.65 | 6.86 |
| Calculated | (% by weight): | 46.39 | 6.95 |

(The calculated values are based on C$_{14}$H$_{25}$O$_3$S$_2$F$_3$(MW: 62.4649)

Starting Temperature of Thermal Decomposition: 164° C.

EXAMPLE 8

Transmittance measurement on a resin film containing an alkylsulfonium salt:

Film-forming procedures and resolution experiments as described below were carried out under a yellow lamp.

1.5 g of poly(methyl methacrylate) having a weight-average molecular weight of 12,000 which was manufactured by Aldrich Chemical Company (hereinafter referred to as "PMMA") and 0.079 g of the alkylsulfonium salt which was prepared in Example 1, 2, 5, 6 or 7 were dissolved in 6 g of ethyl cellosolve acetate and filtered through a membrane filter having 0.2 μm pore size. The resulting filtrate was spin-coated on a 3-inch quartz (silica) substrate and the spin coating film thus formed was baked on a hot plate at 100° C. for 120 seconds. Thus, there were obtained five kinds of thin films each having a thickness of around 1 μm. Dependence of transmittance of the thin films thus obtained on wavelengths was determined using an ultraviolet visible spectrophotometer of UV-365 type which was manufactured by Shimadzu Co. The results are shown in FIG. 1.

For comparison with these films, a film of PMMA alone and a film in which the above alkylsulfonium salt was replaced with a known triphenylsulfonium trifluoromethanesulfonate compound (hereinafter referred to as "TPS") were prepared in the same manner as mentioned above. Measured spectra on the films under the same conditions are shown also in FIG. 1.

It can be seen from this example that the TPS-containing PMMA film has extremely reduced transmittance at the wavelength region of 220 nm or less whereas the films containing the alkylsulfonium salts of examples of the present invention have high transmittance and thus that the alkylsulfonium salts of the present invention are effective as materials of chemically amplified resists for use in lithography in which an exposure wavelength is not more than 220 nm.

EXAMPLE 9

An amount of photoacid generated from an alkylsulfonium salt in acetonitrile when was irradiated with ArF excimer laser beams (193 nm) and its efficiency were measured as mentioned below.

First, 0.3 ml of a solution of the alkylsulfonium salt of Example 1 or TPS in acetonitrile (1×10$^{-2}$ mol·l$^{-1}$) was put in a synthesized quartz cell having a cell length of 1 mm (GL Science Co.). Then, the cell was irradiated with ArF excimer laser beams (HE-460-SM-A type excimer laser manufactured by NEC Co.) at room temperature (exposure area: 3 cm$^2$). After irradiation, the exposed solution was added to an acetonitrile solution containing sodium salt of tetrabromophenol blue as an indicator. Visible light absorption spectra were measured on the resulting solution. An amount of acids thus obtained was determined on the basis of change in absorbance at 619 nm according to the method described in the Analytical Chemistry, Vol. 48, No. 2, 450–451 (1976), the disclosure of which is hereby incorporated by reference herein. The measured results are shown in the following Table 2.

TABLE 2

| Photoacid Generator | Amount of Acid Generated (nmol)* | Quantum Yield |
|---|---|---|
| Compound of Example 1 | 67.4 | 0.348 |
| TPS | 48.8 | 0.249 |

*Exposure amount: 40 mJ · cm$^{-2}$

It can be seen from the above results that the alkylsulfonium salt of the present invention as effective as the photoacid generator.

EXAMPLE 10

An amount of photoacid generated from an alkylsulfonium salt-containing PMMA film (film thickness of 1.0 μm) which was irradiated with ArF excimer laser beams (193 nm) and its efficiency were measured as mentioned below.

As for the photoacid generator, the alkylsulfonium salts of Examples 1 to 7 were used. An amount of each of the alkylsulfonium salts to be used was 5 wt. % based on PMMA. Each of thin films which was formed on a 3-inch silicon wafer in the same manner as in Example 8 was irradiated with ArF excimer laser beams having a center wavelength of 193.3 nm (EX-700 manufactured by Lumonics Co.). In this case, an exposure amount was 40 mJ·cm$^{-2}$ and an exposure area was 20 cm$^2$. After irradiation, the respective thin films were dissolved in acetonitrile. The respective solutions were added to an acetonitrile solution containing a sodium salt of tetrabromophenol blue as an indicator and then visible light absorption spectra were measured on the respective solutions. An amount of acids thus generated was determined on the basis of change in absorbance at 619 nm according to the method described in Analytical Chemistry, Vol. 48, No. 2, 450–451 (1976), as mentioned in Example 9. With regard to the relation between molar number of acid and absorbance, calibration was previously made from absorbances of the known amounts of p-toluenesulfonic acid and the acetonitrile solution as an indicator, and the calibration curve was used in the determination of acid. The measured results are shown in the following Table 3.

TABLE 3

| Photoacid Generator | Amount of Acid generated(n mol) |
| --- | --- |
| Example 1 | 14.0 |
| Example 2 | 2.0 |
| Example 3 | 13.2 |
| Example 4 | 13.5 |
| Example 5 | 10.9 |
| Example 6 | 11.0 |
| Example 7 | 1.0 |

It can be seen from the above results that the alkylsulfonium salts in the present invention are effective as the photoacid generator. In particular, it is believed that ketone group (2-oxocycloalkyl group) structure in the alkylsulfonium salt compound dramatically enhances the photoacid generation efficiency due to the deep ultraviolet light such as ArF excimer laser beams or the like. Thus, the alkylsulfonium salt compound having such ketone group is more preferable.

Referential Example 1

Preparation of poly(tricyclo[5.2.1.0$^{2,6}$]decanyl methacrylate-co-tert-butyl methacrylate):

10 ml of a solution of 2,2-azobis(isobutyronitrile) 0.48 g (0.003 mol) in toluene was added to 120 ml of a toluene solution of tricyclo[5.2.1.0$^{2,6}$]decanyl methacrylate 21.80 g (0.10 mol) and tert-butyl methacrylate 8.80 g (0.05 mol). Thereafter, these monomers were subjected to polymerization reaction at 70° C. for one hour. After the temperature of reaction mixture was returned to room temperature, the reaction-mixture was poured into 1 liter of methanol. Precipitate was recovered by sucking filtration and washed by methanol. After the washing and filtration procedures were repeated three times, the precipitate thus recovered was dried under reduced pressure to obtain 14.52 g (yield: 48.4%) of poly(tricyclo[5.2.1.0$^{2,6}$]decanyl methacrylate-co-tert-butyl methacrylate), being white powder. A tricyclo [5.2.1.0$^{2,6}$]decanyl methacrylate unit and tert-butyl methacrylate unit in the final product was in the ratio 65:35. This copolymerization ratio was determined on the basis of 1H-NMR measurements. The product had weight-average molecular weight of 53,000 (on a polystyrene basis) which was determined on the basis of GPC measurements.

EXAMPLE 11

An ArF contact exposure experiment using a photo-resist composition according to the present invention:

The following experiment was carried out under a yellow lamp.

First, a resist material comprising the following composition was prepared:

| | |
| --- | --- |
| (a) poly(tricyclo[5.2.1.0$^{2,6}$]decanyl methacrylate-co-tert-butyl methacrylate) (resin: the polymer of Referential Example 1): | 2.85 g |
| (b) cyclohexylmethyl(2-oxocyclohexyl)sulfonium trifluoromethanesulfonate (photoacid generator: the compound of (Example 1): | 0.15 g |
| (c) cyclohexanone (solvent): | 12.00 g |

Figure 2A:
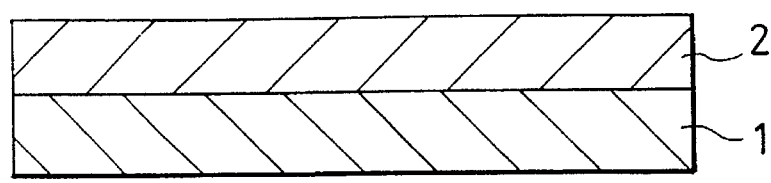
FIGS. 2A to 2C show a series of partially and schematically cross-sectional views for explaining a process of forming a positive type pattern using a photoresist composition of the present invention.
Figure 2B:
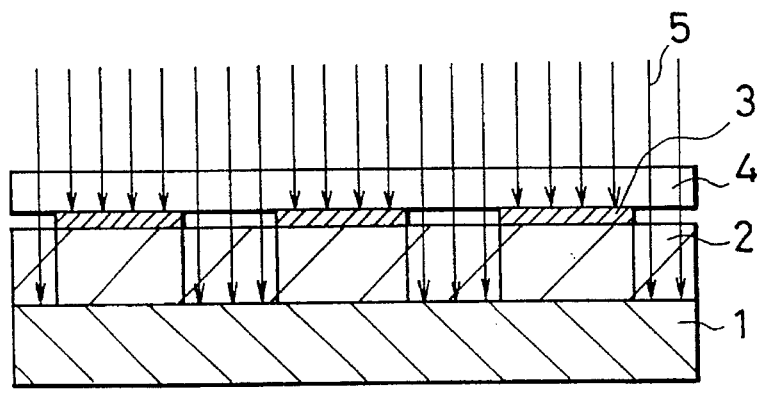
Figure 2C:
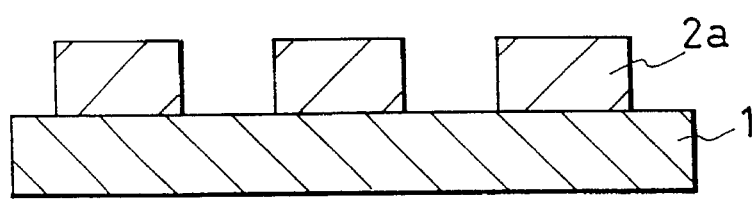
Figure 3:
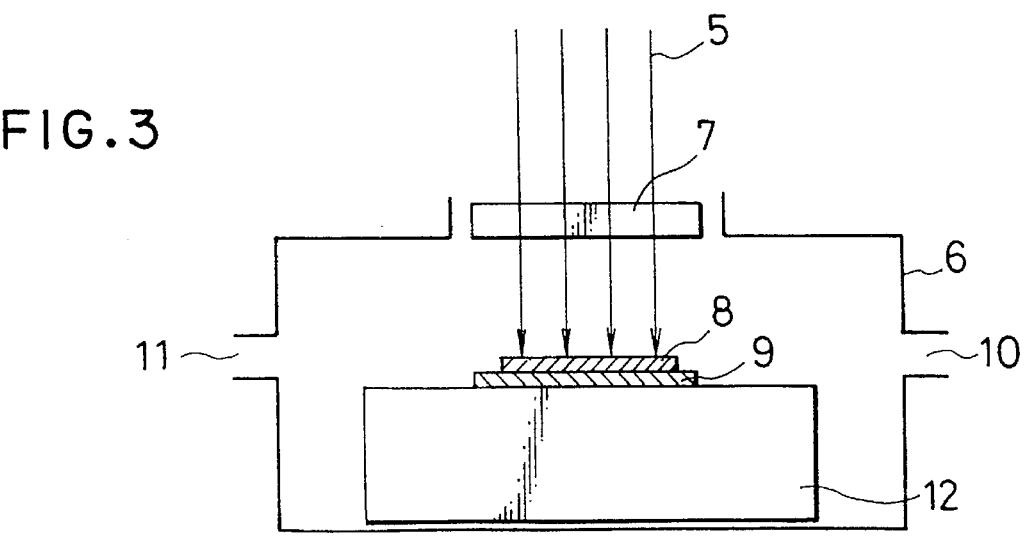
FIG. 3 shows a schematic illustration of a simple laboratory light exposure apparatus as used in an exposure experiment described in Example 9.

The above mixture was filtered through a 2 µm Teflon filter to prepare the resist material. A method of forming a pattern will be described below with reference to FIGS. 2A to 2C and 3. FIGS. 2A to 2C show a series of partially and schematically cross-sectional views for explaining a process of forming a positive type pattern by using a photoresist composition of the present invention and FIG. 3 shows a schematic illustration of a simple laboratory light exposure apparatus to be used in this Example. The laboratory light exposure apparatus comprises a glove box 6, a homogenizer 7 provided with the top of the glove box through which the exposure light is introduced, a nitrogen intake vent 10 and a nitrogen exhaust vent 11 which are provided on side walls of the glove box, and a X-Y stage 12 for placing and fixing a substrate 1 (a wafer 9) which is disposed in the glove box.

Referring to now FIG. 2A, the above resist material was spin-coated on a 3-inch silicon substrate 1 and then baked on a hot plate at 90° C. for 60 seconds to form a thin resist film 2 having a thickness of 0.7 µm. The thin resist film 2 exhibited high transmittance of 73.2% per 1 µm thick and thus it can be said that transparency of the film is sufficiently high as a single-layer resist. Then, as shown in FIG. 3, a wafer 9 consisting of the substrate 1 and the thin resist film 2 formed thereon was placed and fixed on the X-Y stage 12 in the simple laboratory light exposure apparatus which was thoroughly purged with nitrogen. Thereafter, as shown in FIG. 3, a mask 8 with a pattern of a chromium member 3 formed on a quartz (silica) plate member 4 was adhered onto the surface of the thin resist film 2 of the wafer 9 and the thin resist film 2 was irradiated through the mask 8 with ArF excimer laser beams 5. As shown in FIG. 2B, the quartz plate member 4 (a transmitting portion) of the patterned mask 8 transmits the laser beams 5 and the chromium member 3 (a portion for cutting off the laser beams) of the patterned mask 8 cuts off the laser beams 5 to protect the thin resist film located therebelow. At the end of irradiation, the thin resist film 2 was baked on a hot plate at 100° C. for 90 seconds, was developed in an alkaline developing solution (an aqueous solution of 2.0 wt. % tetra-methylammonium hydroxide) of 230° C. for 30 seconds and then rinsed for 60 seconds in purified water. As a result, only the portion of the resist film exposed to the beams was dissolved in the developing solution and removed therefrom to form the positive type pattern 2a as shown in FIG. 2C.

In the above-mentioned experiment, resolution property of 0.25 µm line-and-space was obtained when the exposure energy was around 68.5 mJ/cm$^2$.

EXAMPLES 12 TO 18

The same procedures as in Example 11 were repeated to prepare seven resist materials except that the compound of Example 1 as the photoacid generator was replaced with each of the alkylsulfonium salt compounds obtained in Examples 2 to 7 and 1-adamantyldimethylsulfonium trifluoromethanesulfonate, and patterns were formed in the same manner as in Example 11. The experimental conditions and results are shown in Table 4.

Content of the photoacid generator in each of the resist materials is an amount enough to resolve the patterns which is based on the photoacid generation efficiency as shown in Example 10, i.e. an amount of photoacid generated by the same exposure amount. Namely, an amount of the photoacid generator having lower photoacid generation efficiency was more than that of other photoacid generator having higher photoacid generation efficiency.

TABLE 4

| Ex. | Acid Generator | Amount of Acid Generator(g) | Amount of Resin(g) | Exposure Amount (mJ · cm$^{-2}$) | Resolution (μmL&S) |
|---|---|---|---|---|---|
| 12 | Example 2 | 0.60 | 2.40 | 75.4 | 0.40 |
| 13 | Example 3 | 0.18 | 2.82 | 70.0 | 0.25 |
| 14 | Example 4 | 0.18 | 2.82 | 69.5 | 0.25 |
| 15 | Example 5 | 0.21 | 2.79 | 88.4 | 0.25 |
| 16 | Example 6 | 0.21 | 2.79 | 87.2 | 0.30 |
| 17 | Example 7 | 0.60 | 2.40 | 88.5 | 0.50 |
| 18 | AdMe$_2$* | 0.45 | 2.15 | 88.7 | 0.45 |

*AdMe$_2$ is 1-adamantyldimethylsulfonium trifluoromethanesulfonate prepared according to a method described in D. N. Kevill and S. M. Anderson, J. Am. Chem. Soc., 108, 1579–1585 (1986) and has the following formula:

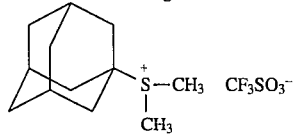

As discussed above, the photoresist composition containing the alkylsulfonium salt in the present invention has high transparency to the radiation such as deep U.V. light having the wavelength region of 220 nm or less, and further exhibits high sensitivity and resolution to the exposure light such as the deep U.V. light. Thus, the resist composition is useful as photoresist which is exposed to light such as the deep U.V. light of 220 nm or less. Furthermore, by using the photoresist composition according to the present invention, it is possible to form fine or densified patterns required to fabricate the semiconductor device.

Furthermore, the novel alkylsulfonium salt in the present invention also has high transparency to the radiation such as deep U.V. light having the wavelength region of 220 nm or less, and further generates effectively a protonic acid by exposure of the compound to the radiation such as the deep U.V. light or the like, as mentioned above. Thus, the compound is useful as photosensitizer (i.e. photoacid generator) for use in the photoresist for the deep U.V. light (particularly, light of shorter wavelengths of 220 nm or less).

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An alkylsulfonium salt compound represented by the following general formula (I):

wherein $R^1$ is a radical selected from the group consisting of linear, branched and cyclic $C_1$ to $C_8$ alkyl radicals, $R^2$ is a $C_5$ to $C_7$ cyclic alkyl radical, said $R^1$ and $R^2$ may be the same or different and $R^3$ is a $C_5$ to $C_7$ 2-oxocycloalkyl radical and $Y^-$ is a counter ion selected from the group consisting of $BF_4^-$, $AsF_6^-$, $SbF_6^-$, $PF_6^{31}$, $CF_3^-SO_3^-$, $Cl^-$, $Br^-$, $I^-$, $ClO_4^-$ and $CH_3SO_3^-$.

2. The alkylsulfonium salt compound as defined in claim 1, wherein said $C_1$–$C_8$ alkyl radical of said $R^1$ is a radical selected from the group consisting of methyl, ethyl, n-propyl, i-propyl, n-butyl, i-butyl, sec-butyl, tert-butyl, pentyl, hexyl, heptyl, octyl, cyclopentyl, cyclohexyl, cycloheptyl, cyclopropylmethyl, 4-methylcyclohexyl and cyclohexylmethyl radicals.

3. The alkylsulfonium salt compound as defined in claim 1, wherein said $C_5$–$C_7$ cyclic alkyl radical of $R^2$ is a radical selected from the group consisting of cyclopentyl, cyclohexyl, cycloheptyl, 4-methylcyclohexyl and cyclohexylmethyl radicals.

4. The alkylsulfonium salt compound as defined in claim 1, wherein said $C_5$–$C_7$ 2-oxocycloalkyl radical of said $R^3$ is a radical selected from the group consisting of 2-oxocyclopentyl, 2-oxocyclohexyl and 2-oxocycloheptyl radicals.

5. The alkylsulfonium salt compound as defined in claim 1, wherein said $Y^{31}$ is represented by the counter ion of $BF_4^-$.

6. The alkylsulfonium salt compound as defined in claim 1 wherein said $Y^-$ is represented by the counter ion of $AsF_6^-$.

7. The alkylsulfonium salt compound as defined in claim 1 wherein said $Y^-$ is represented by the counter ion of $PF_6^-$.

8. The alkylsulfonium salt compound as defined in claim 1 wherein said $Y^-$ is represented by the counter ion of $PF_6^-$.

9. The alkylsulfonium salt compound as defined in claim 1 wherein said $Y^-$ is represented by the counter ion of $CH_3SO_3^-$.

* * * * *

UNITED STATES PATENT AND TRADEMARK OFFICE
CERTIFICATE OF CORRECTION

PATENT NO. : 5,585,507
DATED : December 17, 1996
INVENTOR(S) : Kaichiro Nakano, Katsumi Maeda, Shigeyuki Iwasa, Etsuo Hasegawa It is certified that error appears in the above-identified patent and that said Letters Patent is hereby corrected as shown below:

Column 1, line 54, delete "$el.$," and insert therefor --al.,--.

Column 2, line 28, delete " "89 " and insert therefor -- '89 --.

Column 8, line 33, delete "(VIIIX)" and insert therefor --(VIII)--.

Column 13, line 51, delete "62.4649" and insert therefor --362.4649))--

Column 16, line 60, delete "230°C" and insert therefor --23°C--.

Column 18, line 13, delete "$PF_6^{31}$" and insert therefor -- $PF_6^-$ --

Signed and Sealed this

Sixth Day of May, 1997

Attest:

BRUCE LEHMAN

*Attesting Officer*   *Commissioner of Patents and Trademarks*